United States Patent
Peng et al.

(10) Patent No.: US 6,969,403 B2
(45) Date of Patent: Nov. 29, 2005

(54) ACCOMMODATIVE INTRAOCULAR LENS

(75) Inventors: Qun Peng, Arlington, TX (US); Yin Yang, Arlington, TX (US); Xiaoxiao Zhang, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/453,995

(22) Filed: Jun. 4, 2003

(65) Prior Publication Data

US 2003/0204256 A1 Oct. 30, 2003

Related U.S. Application Data (62) Division of application No. 10/134,877, filed on Apr. 29, 2002, now Pat. No. 6,695,881.

(51) Int. Cl.⁷ .................................................. A61F 2/16
(52) U.S. Cl. ..................................................... 623/6.34
(58) Field of Search ............................... 623/6.34–6.39, 623/6.43, 6.4

(56) References Cited

U.S. PATENT DOCUMENTS

| | | | |
|---|---|---|---|
| 4,718,904 A | 1/1988 | Thornton | |
| 4,946,469 A | 8/1990 | Sarfarazi | |
| 5,203,789 A | 4/1993 | McDonald | |
| 5,203,790 A | 4/1993 | McDonald | |
| 5,275,623 A | 1/1994 | Sarfarzi | |
| 5,326,347 A | 7/1994 | Cumming | |
| 5,425,759 A | 6/1995 | McDonald | |
| 5,476,514 A | 12/1995 | Cumming | |
| 5,496,366 A | 3/1996 | Cumming | |
| 5,562,731 A | 10/1996 | Cumming | |
| 5,578,081 A | 11/1996 | McDonald | |
| 5,674,282 A | 10/1997 | Cumming | |
| 5,769,889 A | 6/1998 | Kelman | |
| 5,824,074 A | 10/1998 | Koch | |
| 5,843,188 A | 12/1998 | McDonald | |
| 5,964,802 A | * 10/1999 | Anello et al. | 623/6.4 |
| 6,197,058 B1 | 3/2001 | Portney | |
| 6,197,059 B1 | 3/2001 | Cumming | |

(Continued)

FOREIGN PATENT DOCUMENTS

| | | |
|---|---|---|
| JP | 2-126847 | 5/1990 |
| WO | WO 99/47185 | 9/1999 |
| WO | WO 00/61036 | 10/2000 |
| WO | WO 00/66037 | 11/2000 |
| WO | WO 01/19288 | 3/2001 |
| WO | WO 01/19829 | 3/2001 |
| WO | WO 01/34067 | 5/2001 |
| WO | WO 01/66041 | 9/2001 |
| WO | WO 01/66042 | 9/2001 |
| WO | WO 02/09620 | 2/2002 |
| WO | WO 03/000154 A2 | 1/2003 |

OTHER PUBLICATIONS

Hara, et al., "Accommodative Intraocular Lens with Spring Action Part 1. Design and Placement in an Excised Animal Eye", Ophthalmic Surgery, Feb. 1990, vol. 21, No. 2, pp. 128–133.

Hara, et al., "Accommodative Intraocular Lens with Spring Action Part 2. Fixation in the Living Rabbit", Ophthalmic Surgery, Sepember 1992, vol. 23, No. 9, pp. 632–635.

*Primary Examiner*—Suzette J-J Gherbi
(74) *Attorney, Agent, or Firm*—Jeffrey S. Schira (57) ABSTRACT

A two-optic accommodative lens system. The first lens has a negative power and is located posteriorly against the posterior capsule. The periphery of the first optic contains a pair of clasps. The second optic is located anteriorly to the first optic and is of a positive power. The peripheral edge of the second optic contains a pair of locking arms that fit into the clasps contained on the periphery of the first optic to lock the second optic onto the first optic, but allow for rotation of the arms within the clasps. Hinge structures on the locking arms allow the second optic to move relative to the first optic along the optical axis of the lens system in reaction to movement of the ciliary muscle.

10 Claims, 7 Drawing Sheets

U.S. PATENT DOCUMENTS

| | | |
|---|---|---|
| 6,217,612 B1 | 4/2001 | Woods |
| 6,241,777 B1 | 6/2001 | Kellan |
| 6,261,321 B1 | 7/2001 | Kellan |
| 6,299,641 B1 | 10/2001 | Woods |
| 6,302,911 B1 | 10/2001 | Hanna |
| 6,342,073 B1 | 1/2002 | Cumming et al. |
| 6,387,126 B1 | 5/2002 | Cumming |
| 6,406,494 B1 | 6/2002 | Laguette et al. |
| 6,423,094 B1 | 7/2002 | Sarfarazi |
| 6,454,801 B1 | 9/2002 | Portney |
| 6,464,725 B2 | 10/2002 | Skotton |
| 6,488,708 B2 | 12/2002 | Safarazi |
| 6,494,911 B2 * | 12/2002 | Cumming .................. 623/6.37 |
| 6,558,420 B2 * | 5/2003 | Green ....................... 623/6.34 |
| 6,616,691 B1 * | 9/2003 | Tran .......................... 623/6.11 |
| 6,616,692 B1 * | 9/2003 | Glick et al. ................ 623/6.34 |
| 6,695,881 B2 * | 2/2004 | Peng et al. ................ 623/6.34 |
| 2002/0002404 A1 | 1/2002 | Sarfarazi |
| 2002/0035398 A1 | 3/2002 | Cumming |
| 2002/0045937 A1 | 4/2002 | Sarfarazi |
| 2002/0055777 A1 | 5/2002 | Cumming et al. |
| 2002/0068971 A1 | 6/2002 | Cumming |
| 2002/0107568 A1 | 8/2002 | Zadno-Azizi et al. |
| 2002/0143395 A1 | 10/2002 | Skottun |

* cited by examiner

ACCOMMODATIVE INTRAOCULAR LENS

This application is a divisional of U.S. patent application Ser. No. 10/134,877, filed Apr. 29, 2002 now U.S. Pat. No. 6,695,881.

BACKGROUND OF THE INVENTION

This invention relates generally to the field of intraocular lenses (IOL) and, more particularly, to accommodative IOLs.

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

In the natural lens, bifocality of distance and near vision is provided by a mechanism known as accommodation. The natural lens, early in life, is soft and contained within the capsular bag. The bag is suspended from the ciliary muscle by the zonules. Relaxation of the ciliary muscle tightens the zonules, and stretches the capsular bag. As a result, the natural lens tends to flatten. Tightening of the ciliary muscle relaxes the tension on the zonules, allowing the capsular bag and the natural lens to assume a more rounded shape. In the way, the natural lens can be focus alternatively on near and far objects.

As the lens ages, it becomes harder and is less able to change shape in reaction to the tightening of the ciliary muscle. This makes it harder for the lens to focus on near objects, a medical condition known as presbyopia. Presbyopia affects nearly all adults over the age of 45 or 50.

Prior to the present invention, when a cataract or other disease required the removal of the natural lens and replacement with an artificial IOL, the IOL was a monofocal lens, requiring that the patient use a pair of spectacles or contact lenses for near vision. Allergan has been selling an bifocal IOL, the Array lens, for several years, but due to quality of issues, this lens has not been widely accepted.

Several designs for accommodative IOLs are being studied. For example, several designs manufactured by C&C Vision are currently undergoing clinical trials. See U.S. Pat. Nos. 6,197,059, 5,674,282, 5,496,366 and 5,476,514 (Cumming), the entire contents of which being incorporated herein by reference. The lens described in these patents is a single optic lens having flexible haptics that allows the optic to move forward and backward in reaction to movement of the ciliary muscle. A similar designs are described in U.S. Pat. No. 6,302,911 B1 (Hanna), U.S. Pat. Nos. 6,261,321 B1 and 6,241,777 B1 (both to Kellan), the entire contents of which being incorporated herein by reference. The amount of movement of the optic in these single-lens systems, however, may be insufficient to allow for a useful range of accommodation. In addition, as described in U.S. Pat. Nos. 6,197,059, 5,674,282, 5,496,366 and 5,476,514, the eye must be paralyzed for one to two weeks in order for capsular fibrosis to entrap the lens that thereby provide for a rigid association between the lens and the capsular bag. In addition, the commercial models of these lenses are made from a hydrogel or silicone material. Such materials are not inherently resistive to the formation of posterior capsule opacification ("PCO"). The only treatment for PCO is a capsulotomy using a Nd:YAG laser that vaporizes a portion of the posterior capsule. Such destruction of the posterior capsule may destroy the mechanism of accommodation of these lenses.

There have been some attempts to make a two-optic accommodative lens system. For example, U.S. Pat. No. 5,275,623 (Sarfarazi), WIPO Publication No. 00/66037 (Glick, et al.) and WO 01/34067 A1 (Bandhauer, et al), the entire contents of which being incorporated herein by reference, all disclose a two-optic lens system with one optic having a positive power and the other optic having a negative power. The optics are connected by a hinge mechanism that reacts to movement of the ciliary muscle to move the optics closer together or further apart, thereby providing accommodation. In order to provide this "zoom lens" effect, movement of the ciliary muscle must be adequately transmitted to the lens system through the capsular bag, and none of these references disclose a mechanism for ensuring that there is a tight connection between the capsular bag and the lens system. In addition, none of these lenses designs have addressed the problem with PCO noted above.

Therefore, a need continues to exist for a safe and stable accommodative intraocular lens system that provides accommodation over a broad and useful range.

BRIEF SUMMARY OF THE INVENTION

The present invention improves upon the prior art by providing a two-optic accommodative lens system. The first lens has a negative power and is located posteriorly against the posterior capsule. The periphery of the first optic contains a pair of clasps. The second optic is located anteriorly to the first optic and is of a positive power. The peripheral edge of the second optic contains a pair of locking arms that fit into the clasps contained on the periphery of the first optic to lock the second optic onto the first optic, but allow for rotation of the arms within the clasps. Hinge structures on the locking arms allow the second optic to move relative to the first optic along the optical axis of the lens system in reaction to movement of the ciliary muscle.

Accordingly, one objective of the present invention is to provide a safe and biocompatible intraocular lens.

Another objective of the present invention is to provide a safe and biocompatible intraocular lens that is easily implanted in the posterior chamber.

Still another objective of the present invention is to provide a safe and biocompatible intraocular lens that is stable in the posterior chamber.

Still another objective of the present invention is to provide a safe and biocompatible accommodative lens system.

These and other advantages and objectives of the present invention will become apparent from the detailed description and claims that follow.

DETAILED DESCRIPTION OF THE INVENTION

As best seen in FIGS. 1–5 and 10, lens system 10 of the present invention generally consists of posterior optic 12 and anterior optic 14. Optic 12 is preferably formed in any suitable overall diameter or length, for example, around 12 millimeters, for implantation in the posterior chamber. Optic 12 preferably is made from a soft, foldable material that is inherently resistive to the formation of PCO, such as a soft acrylic. Optic 14 preferable is made from a soft, foldable material such as a hydrogel, silicone or soft acrylic. Optic 12 may be any suitable power, but preferably has a negative power. Optic 14 may also be any suitable power but preferably has a positive power. The relative powers of optics 12 and 14 should be such that the axial movement of optic 14 toward or away from optic 12 should be sufficient to adjust the overall power of lens system 10 at least one diopter and preferably, at least three to four diopters, calculation of such powers of optics 12 and 14 being within the capabilities of one skilled in the art of designing ophthalmic lenses by, for example, using the following equations:

$$P = P_1 + P_2 - T/n * P_1 P_2 \quad (1)$$

$$\delta P = \delta T/n * P_1 P_2 \quad (2)$$

Figure 1:
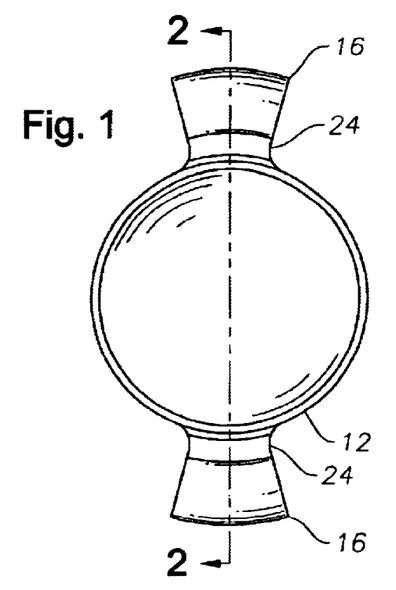
FIG. 1 is an enlarged top plan view of the first optic of a first embodiment of the lens system of the present invention.
Figure 2:
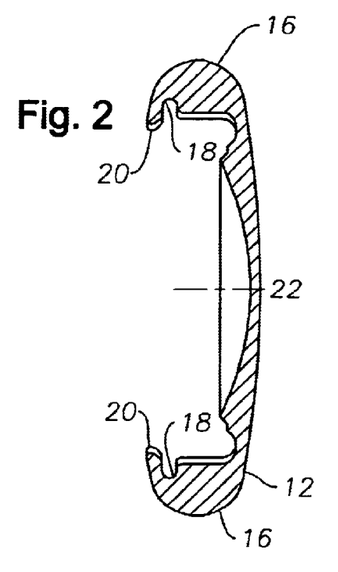
FIG. 2 is an enlarged cross-sectional view of the first optic of a first embodiment of the lens system of the present invention taken at line 2—2 in FIG. 1.
Figure 3:
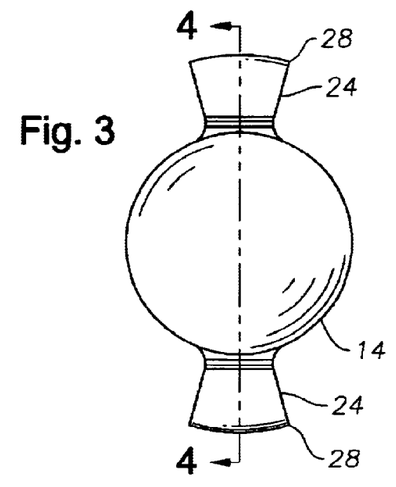
FIG. 3 is an enlarged top plan view of the second optic of a first embodiment of the lens system of the present invention.
Figure 4:
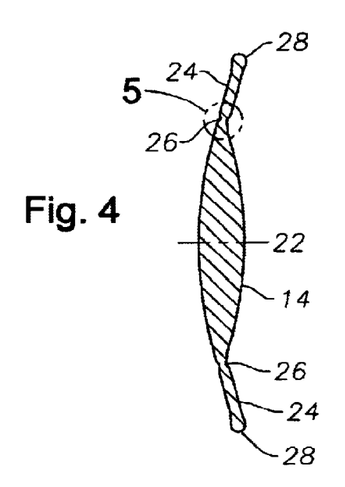
FIG. 4 is an enlarged cross-sectional view of the second optic of a first embodiment of the lens system of the present invention taken at line 4—4 in FIG. 3.
Figure 5:
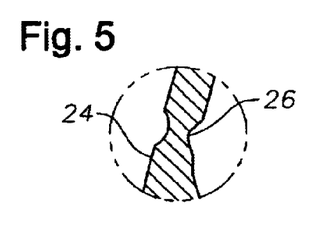
FIG. 5 is an enlarged partial cross-sectional view taken at circle 5 in FIG. 4.
Figure 10:
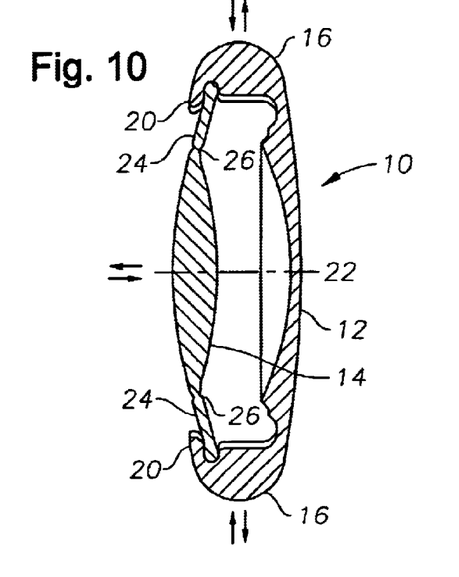
FIG. 10 is a cross-sectional view of the first embodiment of the lens system of the present invention illustrated in FIGS. 1–5.

As best seen in FIGS. 1 and 2, optic 12 is generally symmetrical about optical axis 22 and contains a pair of opposing clasps 16 that are shaped to stretch and fill equatorial region 210 of capsular bag 200. Clasps 16 contain sockets 18 generally defined by latch 20. As best seen in FIGS. 3–5, optic 14 contains a pair of haptics 24 that are connected to optic 14 by hinge regions 26 and contain locking pins 28 distally from hinge regions 26. As seen in FIG. 10, locking pins 28 are sized and shaped to fit within sockets 18 on optic 12, thereby holding optic 14 firmly within optic 12 while still permitting rotation of locking pins 28 within sockets 18. One skilled in the art will recognize that sockets 18 may be located on hinge regions 26 and that locking pins 28 may be located on optic 12. In order to insert locking pins 28 within sockets 18, sockets 18 may be spread apart slightly, thereby preloading haptics 24. Once implanted in an eye, as one skilled in the art will recognize, contraction of capsular bag 200 will cause clasps 16 to collapse slightly, thereby causing compression of optic 14. As optic 14 is compressed, hinge regions 26 allow optic 14 to vault anteriorly away from optic 12, with locking pins 28 pivoting within sockets 18. One skilled in the art will recognize that no specific feature needs to be used to form hinge regions 26 as haptics 24 may be formed from a material and/or in such a configuration that haptics naturally flex in the manner of a hinge.

As best seen in FIGS. 6–9 and 11, lens system 110 of the present invention generally consisting of posterior optic 112 and anterior optic 114. Optic 112 is preferably formed in any suitable overall diameter or length, for example, around 12 millimeters, for implantation in the posterior chamber. Optic 112 preferably is made from a soft, foldable material that is inherently resistive to the formation of PCO, such as a soft acrylic. Optic 114 preferable is made from a soft, foldable material such as a hydrogel, silicone or soft acrylic. Optic 112 may be any suitable power, but preferably has a negative power. Optic 114 may also be any suitable power but preferably has a positive power. The relative powers of optics 112 and 114 should be such that the axial movement of optic 114 toward or away from optic 112 should be sufficient to adjust the overall power of lens system 10 at least one diopter and preferably, at least three to four diopters, calculation of such powers of optics 112 and 114 being within the capabilities of one skilled in the art. One skilled in the art will also recognize that the axial movement of optic 114 relative to optic 112 is greater in this embodiment as opposed to the embodiment illustrated in FIGS. 1–5 due to the longer length of haptic 124 versus haptic 24.

Figure 6:
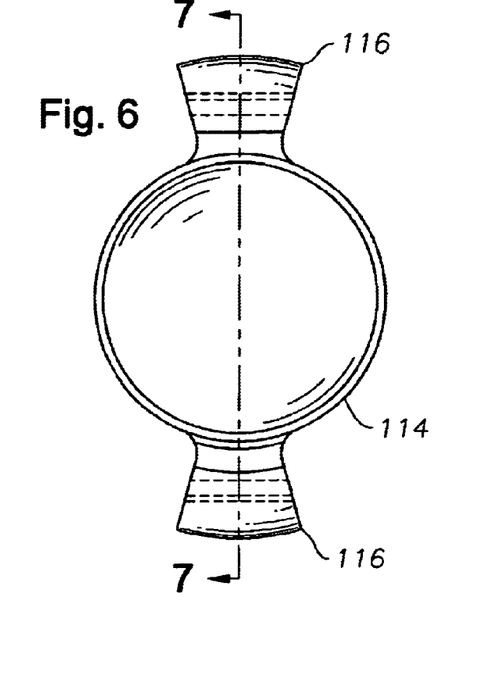
FIG. 6 is an enlarged top plan view of the first optic of a second embodiment of the lens system of the present invention.
Figure 7:
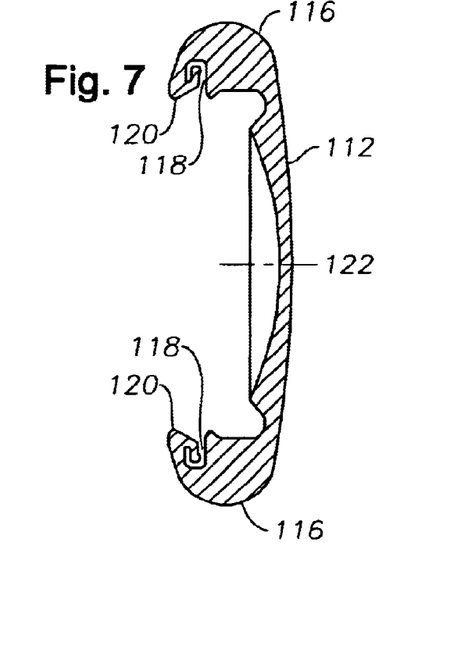
FIG. 7 is an enlarged cross-sectional view of the first optic of a second embodiment of the lens system of the present invention taken at line 7—7 in FIG. 6.
Figure 8:
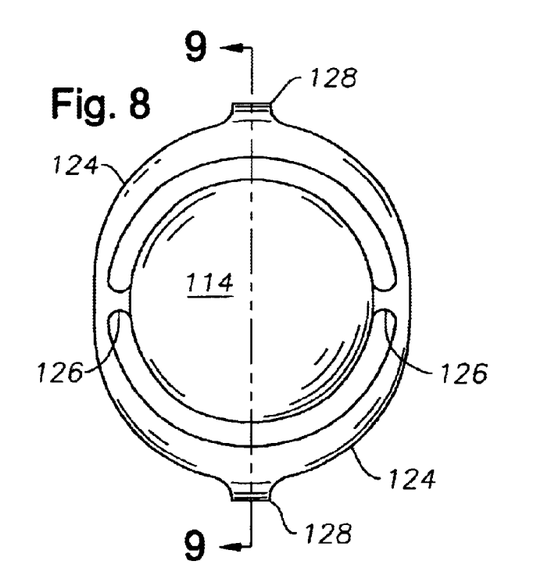
FIG. 8 is an enlarged top plan view of the second optic of a second embodiment of the lens system of the present invention.
Figure 9:
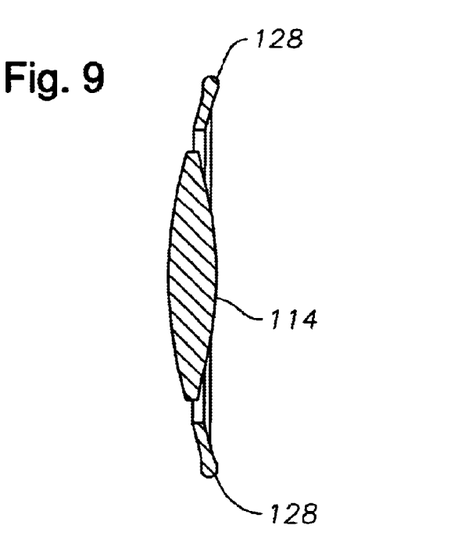
FIG. 9 is an enlarged cross-sectional view of the second optic of a second embodiment of the lens system of the present invention taken at line 9—9 in FIG. 8.
Figure 11:
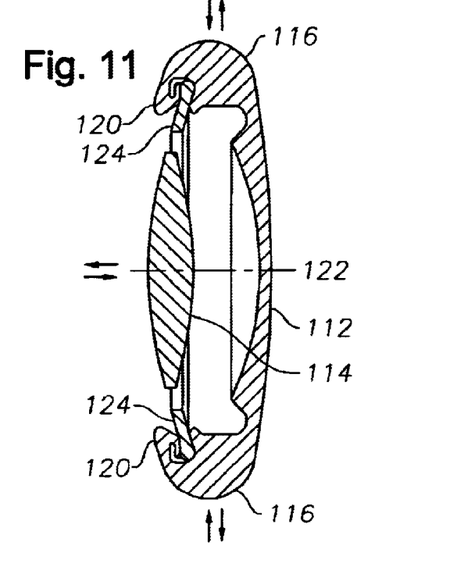
FIG. 11 is a cross-sectional view of the second embodiment of the lens system of the present invention illustrated in FIGS. 6–9.
Figure 13:
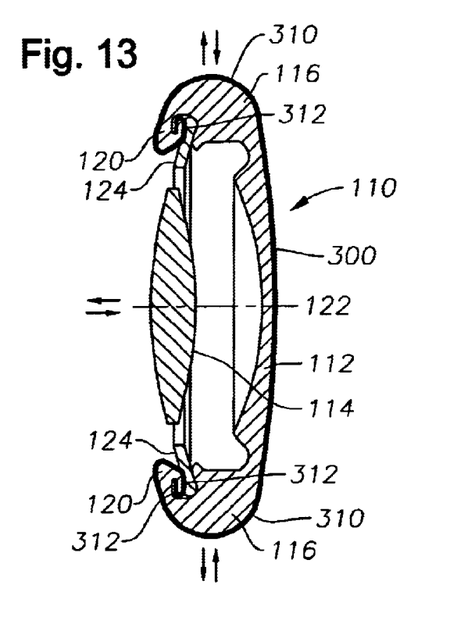
FIG. 13 is a cross-sectional view of the second embodiment of the lens system of the present invention illustrated in FIGS. 6–9 and illustrating the lens system implanted within a capsular bag.
Figure 14:
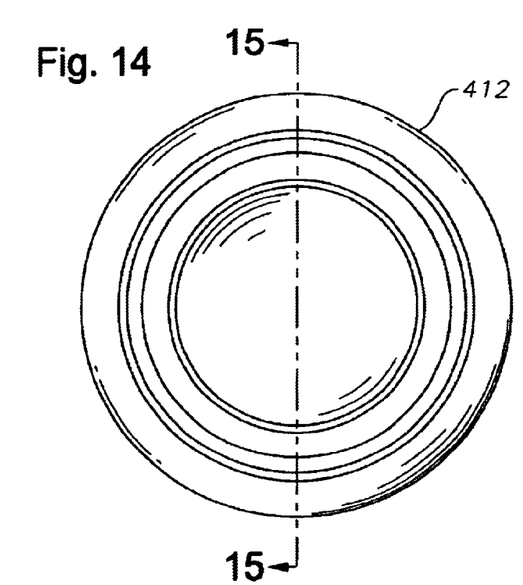
FIG. 14 is an enlarged top plan view of the first optic of a third embodiment of the lens system of the present invention.

As best seen in FIGS. 6, 7 and 13, optic 112 is generally symmetrical about optical axis 122 and contains a pair of opposing clasps 116 that are shaped to stretch and fill equatorial region 310 of capsular bag 300. Clasps 116 contain sockets 118 generally defined by latch 120. As best seen in FIGS. 8 and 9, optic 114 contains circumferential haptic 124 that are connected to optic 114 by hinge regions 126 and contain locking pins 128 distally on the periphery of haptics 124. One skilled in the art will recognize that sockets 118 may be located on clasps 116 and that locking pins 128 may be located on haptics 124. As seen in FIG. 11, locking pins 128 are sized and shaped to fit within sockets 118 on optic 112, thereby holding optic 114 firmly within optic 112 while still permitting rotation of locking pins 128 within sockets 118. Preferably, locking pins 128 are located approximately 90° from hinge regions 126 around the circumference of optic 114. In order to insert locking pins 128 within sockets 118, sockets 118 may be spread apart slightly, thereby preloading haptics 124. One skilled in the art will recognize that no specific feature needs to be used to form hinge regions 126 as haptics 124 may be formed from a material and/or in such a configuration that haptics naturally flex in the manner of a hinge.

Once implanted in an eye, as one skilled in the art will recognize, contraction of capsular bag 300 will cause clasps 116 to collapse slightly, thereby causing compression of optic 114. As optic 114 is compressed, hinge regions 126 allow optic 114 to vault anteriorly away from optic 112, with locking pins 128 pivoting within sockets 118.

Figure 12:
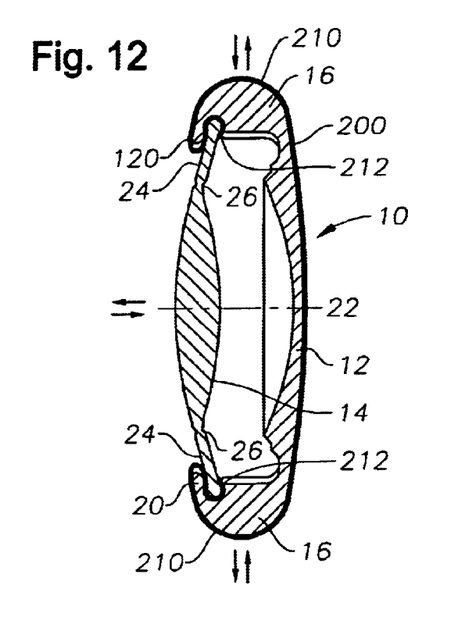
FIG. 12 is a cross-sectional view of the first embodiment of the lens system of the present invention illustrated in FIGS. 1–5 and illustrating the lens system implanted within a capsular bag.

As best seen in FIGS. 12 and 13, lens system 10 and 110 fills capsular bag 200 and 300, respectively, following removal of the natural lens. In order to remove the natural lens, an opening or rhexis is normally made in the anterior side of capsule 200 or 300. The opening contains rim or margin 212 or 312 During implantation of system 10 or 110, rim or margin 212 or 312 is inserted into socket 18 or 118 prior to the introduction of optic 14 or 114, respectively. Once optic 14 or 114 is installed in optic 12 or 112, locking pins 28 and 128 help to contain rim 212 or 312 within sockets 18 or 118, respectively, thereby maintaining a positive mechanical connection between capsular bag 200 and 300 and lens system 10 and 110, respectively. Contraction of capsular bag 200 or 300 will therefore be more directly translated into contraction of optics 12 and 112, respectively. In addition, the self-locking design of sockets 18 and 118 prevent capsular bag 200 and 300 from slipping out of sockets 18 or 118, respectively.

As best seen in FIGS. 15–21, lens system 410 of the present invention of the present invention generally consists of posterior optic 412 and anterior optic 414. Optic 412 is preferably formed in any suitable overall diameter or length, for example, around 12 millimeters, for implantation in the posterior chamber. Optic 412 preferably is made from a soft, foldable material that is inherently resistive to the formation of PCO, such as a soft acrylic. Optic 414 preferable is made from a soft, foldable material such as a hydrogel, silicone or soft acrylic. Optic 412 may be any suitable power, but preferably has a negative power. Optic 414 may also be any suitable power but preferably has a positive power. The relative powers of optics 412 and 414 should be such that the axial movement of optic 414 toward or away from optic 412 should be sufficient to adjust the overall power of lens system 410 at least one diopter and preferably, at least three to four diopters, calculation of such powers of optics 412 and 414 being within the capabilities of one skilled in the art as described above.

Figure 15:
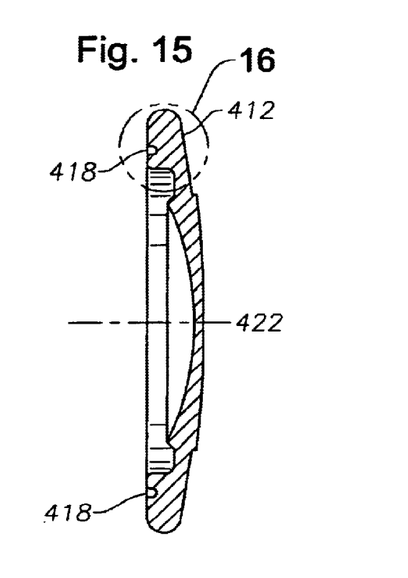
FIG. 15 is an enlarged cross-sectional view of the first optic of a third embodiment of the lens system of the present invention taken at line 15—15 in FIG. 14.
Figure 16:
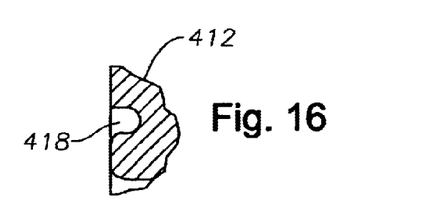
FIG. 16 is an enlarged partial cross-sectional view taken at circle 16 in FIG. 15.
Figure 17:
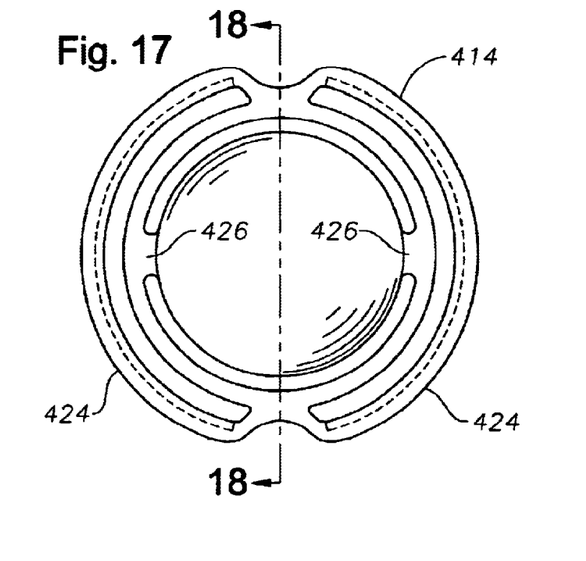
FIG. 17 is an enlarged top plan view of the second optic of a third embodiment of the lens system of the present invention.
Figure 18:
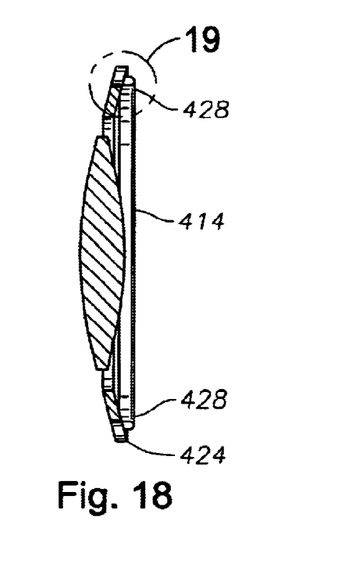
FIG. 18 is an enlarged cross-sectional view of the second optic of a third embodiment of the lens system of the present invention taken at line 18—18 in FIG. 17.
Figure 19:
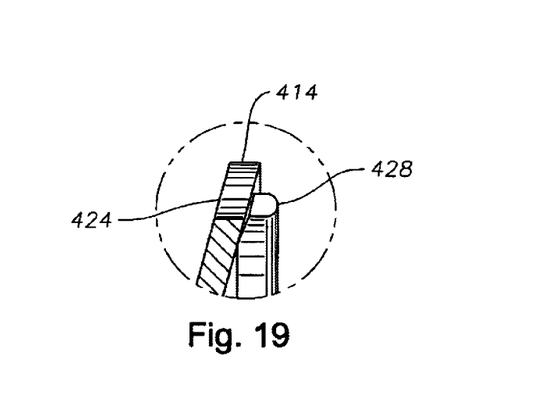
FIG. 19 is an enlarged partial cross-sectional view taken at circle 19 in FIG. 18.
Figure 20:
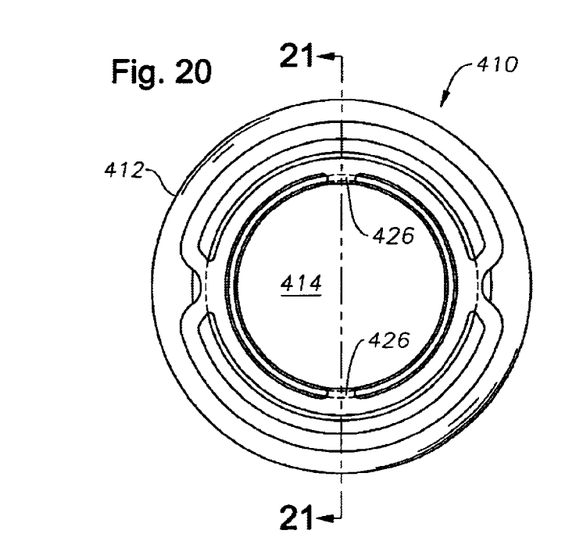
FIG. 20 is an enlarged top plan view of the third embodiment of the lens system of the present invention illustrated in FIGS. 14–19.
Figure 21:
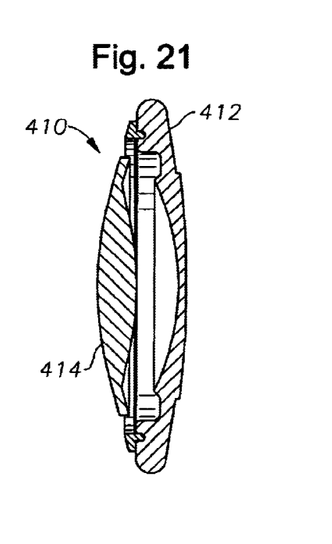
FIG. 21 is a cross-sectional view of the third embodiment of the lens system of the present invention taken at line 21—21 in FIG. 20.

As best seen in FIGS. 15 and 16, optic 412 is generally symmetrical about optical axis 422 and contains a circumferential socket 418. As best seen in FIGS. 17–19, optic 414 contains a pair of hemispherical haptics 424 that are connected to optic 414 by hinge regions 426 and contain circumferential locking rib 428. As seen in FIG. 21, locking rib 428 is sized and shaped to fit within socket 418 on optic 412, thereby holding optic 414 firmly within optic 412 while allowing rotation of locking rib 428 within socket 418. Once implanted in an eye, as one skilled in the art will recognize, contraction of the capsular bag will cause compression of optic 414. As optic 414 is compressed, hinge regions 426 allow optic 414 to vault anteriorly away from optic 412, with locking rib 428 pivoting within socket 418.

As best seen in FIGS. 22–28, lens system 510 of the present invention of the present invention is similar to system 510 and generally consists of posterior optic 512 and anterior optic 514. Optic 512 is preferably formed in any suitable overall diameter or length, for example, around 12 millimeters, for implantation in the posterior chamber. Optic 512 preferably is made from a soft, foldable material that is inherently resistive to the formation of PCO, such as a soft acrylic. Optic 514 preferable is made from a soft, foldable material such as a hydrogel, silicone or soft acrylic. Optic 512 may be any suitable power, but preferably has a negative power. Optic 514 may also be any suitable power but preferably has a positive power. The relative powers of optics 512 and 514 should be such that the axial movement of optic 514 toward or away from optic 512 should be sufficient to adjust the overall power of lens system 510 at least one diopter and preferably, at least three to four diopters, calculation of such powers of optics 512 and 514 being within the capabilities of one skilled in the art as described above.

Figure 22:
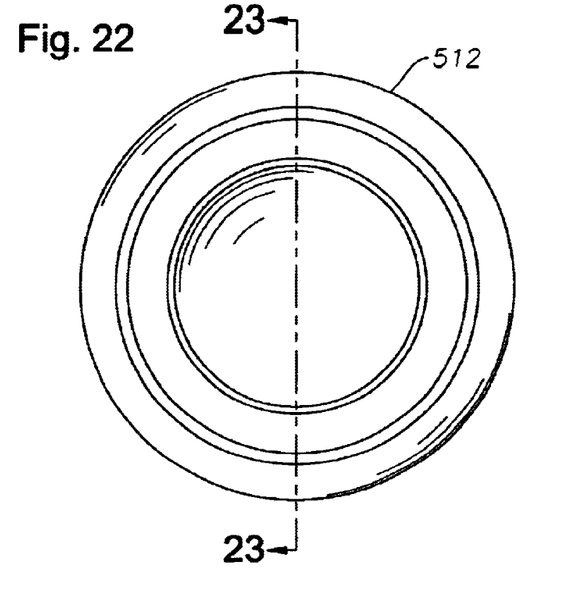
FIG. 22 is an enlarged top plan view of the first optic of a fourth embodiment of the lens system of the present invention.
Figure 23:
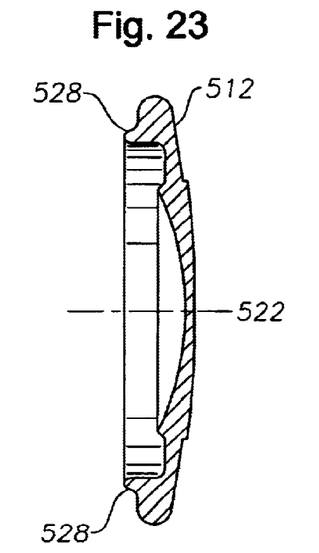
FIG. 23 is an enlarged cross-sectional view of the first optic of a third embodiment of the lens system of the present invention taken at line 23—23 in FIG. 22.
Figure 24:
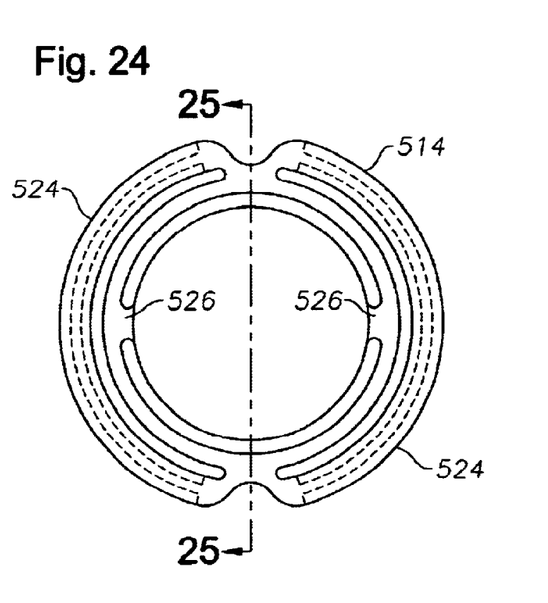
FIG. 24 is an enlarged top plan view of the second optic of a fourth embodiment of the lens system of the present invention.
Figure 25:
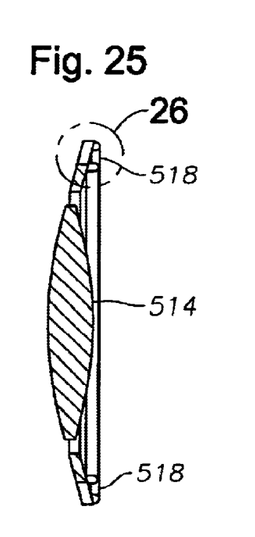
FIG. 25 is an enlarged cross-sectional view of the second optic of a third embodiment of the lens system of the present invention taken at line 25—25 in FIG. 24.
Figure 26:
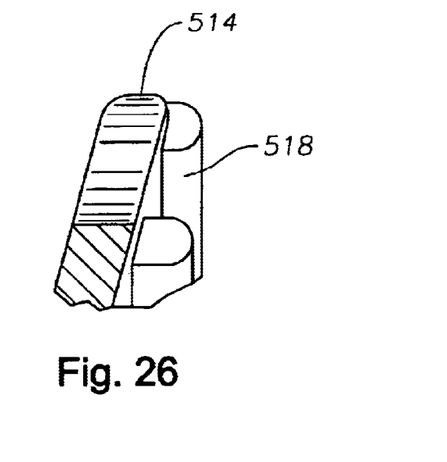
FIG. 26 is an enlarged partial cross-sectional view taken at circle 26 in FIG. 25.
Figure 27:
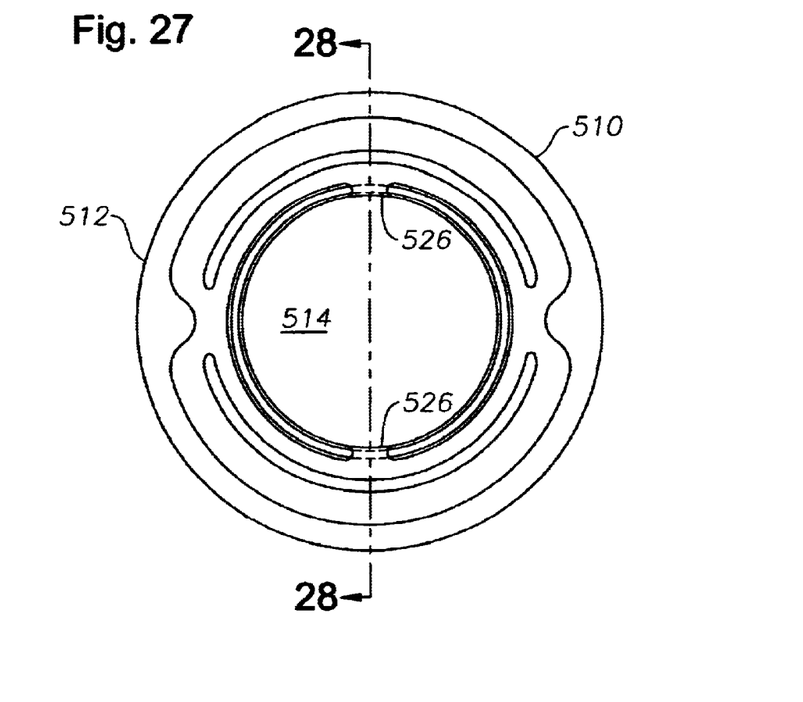
FIG. 27 is an enlarged top plan view of the fourth embodiment of the lens system of the present invention illustrated in FIGS. 26—26.
Figure 28:
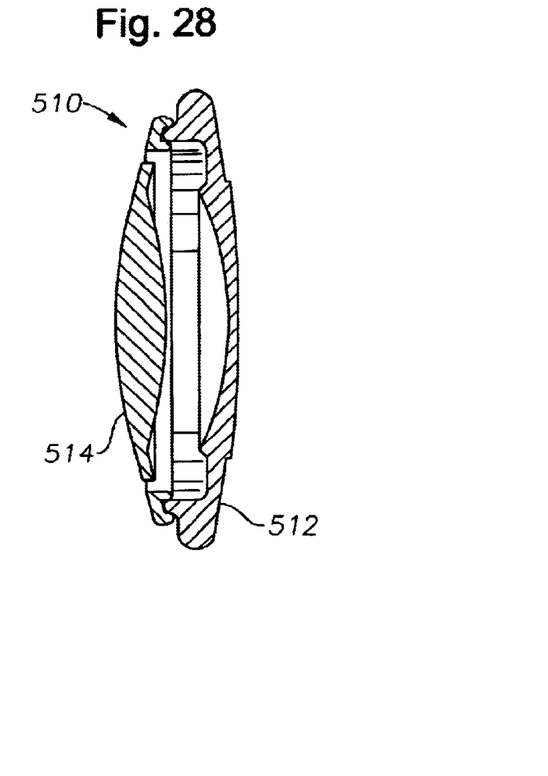
FIG. 28 is a cross-sectional view of the fourth embodiment of the lens system of the present invention taken at line 28—28 in FIG. 27.

As best seen in FIGS. 22 and 23, optic 512 is generally symmetrical about optical axis 522 and contains a circumferential rib 528, which is similar to rib 428 in system 410. As best seen in FIGS. 24–26, optic 514 contains a pair of hemispherical haptics 524 that are connected to optic 514 by hinge regions 526 and contain circumferential socket 518. As seen in FIG. 28, locking rib 528 is sized and shaped to fit within socket 518 on optic 514, thereby holding optic 514 firmly within optic 512 while allowing rotation of locking rib 528 within socket 518. Once implanted in an eye, as one skilled in the art will recognize, contraction of the capsular bag will cause compression of optic 514. As optic 514 is compressed, hinge regions 526 allow optic 514 to vault anteriorly away from optic 512, with locking rib 528 pivoting within socket 518.

This description is given for purposes of illustration and explanation. It will be apparent to those skilled in the relevant art that changes and modifications may be made to the invention described above without departing from its scope or spirit.

We claim:

1. An intraocular lens, comprising:
   a) a first optic having a circumferential socket;
   b) a second optic having at least one haptic, the haptic being connected to the second optic by a hinge region, the hinge region allowing the second optic to vault away from the first optic in reaction to compression of the first optic; and
   c) a circumferential locking rib located on the haptic, the locking rib sized and shaped to be received in the socket and thereby movably attach the second optic to the first optic.

2. The lens of claim 1 wherein the first optic and the second optic comprise a soft acrylic.

3. The lens of claim 1 wherein the second optic comprises a hydrogel.

4. The lens of claim 1 wherein the second optic comprises silicone.

5. The lens of claim 1 wherein the locking rib and socket are sized and shaped to retain an anterior capsular rhexis rim when the locking rib is installed within the socket.

6. An intraocular lens, comprising:
   a) a first optic having a circumferential locking rib;
   b) a second optic having at least one haptic, the haptic being connected to the second optic by a hinge region, the hinge region allowing the second optic to vault away from the first antic in reaction to compression of the first optic; and
   c) a circumferential socket located on the haptic, the socket sized and shaped to receive the locking rib and thereby movably attach the second optic to the first optic.

7. The lens of claim 6 wherein the first optic and the second optic comprise a soft acrylic.

8. The lens of claim 6 wherein the second optic comprises a hydrogel.

9. The lens of claim 6 wherein the second optic comprises silicone.

10. The lens of claim 6 wherein the locking rib and socket are sized and shaped to retain an anterior capsular rhexis rim when the locking rib is installed within the socket.

* * * * *